(12) United States Patent
Jain et al.

(10) Patent No.: US 8,357,196 B2
(45) Date of Patent: Jan. 22, 2013

(54) MARK FOR INTRAOCULAR LENSES

(75) Inventors: Rakhi Jain, Irvine, CA (US); Douglas S. Cali, Mission Viejo, CA (US); Huawei Zhao, Irvine, CA (US); David A. Ruddocks, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 443 days.

(21) Appl. No.: 12/620,765

(22) Filed: Nov. 18, 2009

(65) Prior Publication Data

US 2011/0118836 A1 May 19, 2011

(51) Int. Cl.
*A61F 2/16* (2006.01)

(52) U.S. Cl. .................. 623/6.11; 623/6.14; 623/6.42

(58) Field of Classification Search .................. 623/5.13, 623/6.14, 6.42, 6.11; 351/169, 176
See application file for complete search history.

(56) References Cited

U.S. PATENT DOCUMENTS

| | | | |
|---|---|---|---|
| 3,988,068 A | 10/1976 | Sprague | |
| 4,268,133 A | 5/1981 | Fischer et al. | |
| 4,316,292 A | 2/1982 | Alexeev | |
| 4,343,050 A | 8/1982 | Kelman | |
| 4,449,257 A | 5/1984 | Koeniger | |
| 4,525,044 A | 6/1985 | Bauman | |
| 4,605,409 A | 8/1986 | Kelman | |
| 4,624,669 A * | 11/1986 | Grendahl | 623/5.13 |
| 4,642,114 A | 2/1987 | Rosa | |
| 4,676,791 A | 6/1987 | LeMaster et al. | |
| 4,718,906 A | 1/1988 | Mackool | |
| 4,781,718 A | 11/1988 | Lindstrom | |
| 4,808,181 A | 2/1989 | Kelman | |
| 4,816,032 A * | 3/1989 | Hetland | 623/6.14 |
| 4,863,466 A | 9/1989 | Schlegel | |
| 4,863,470 A | 9/1989 | Carter | |
| 4,898,461 A | 2/1990 | Portney | |
| 4,955,909 A | 9/1990 | Ersek et al. | |
| 4,995,715 A | 2/1991 | Cohen | |
| 5,002,571 A | 3/1991 | O'donnell, Jr. et al. | |
| 5,092,880 A | 3/1992 | Ohmi | |
| 5,203,790 A | 4/1993 | McDonald | |
| 5,219,361 A | 6/1993 | Von Recum et al. | |
| 5,405,385 A | 4/1995 | Heimke et al. | |
| 5,580,498 A | 12/1996 | Sugiyama et al. | |
| 5,755,786 A | 5/1998 | Woffinden et al. | |

(Continued)

FOREIGN PATENT DOCUMENTS

EP 246754 A1 11/1987
EP 1225441 A2 1/2002

(Continued)

OTHER PUBLICATIONS

International Search Report for Application No. PCT/US2010/057016, mailed on Dec. 23, 2010, 5 pages.

(Continued)

*Primary Examiner* — Paul Prebilic
(74) *Attorney, Agent, or Firm* — Abbott Medical Optics Inc.

(57) ABSTRACT

An intraocular lens for providing vision to an animal or human subject has anterior and posterior sides. The lens includes an optic body, one or more haptics, and one or more marks. Each mark has four or more features disposed along an imaginary line when viewed from the anterior side and/or the posterior side. The mark(s) may be used as an aid in angularly aligning the lens during use.

31 Claims, 3 Drawing Sheets

U.S. PATENT DOCUMENTS

| | | | |
|---|---|---|---|
| 5,963,299 A | 10/1999 | Reyburn | |
| 6,024,448 A | 2/2000 | Wu et al. | |
| 6,027,531 A | 2/2000 | Tassignon | |
| 6,042,230 A | 3/2000 | Neadle et al. | |
| 6,079,826 A | 6/2000 | Appleton et al. | |
| 6,129,759 A * | 10/2000 | Chambers | 623/6.17 |
| RE37,071 E | 2/2001 | Gabrielian et al. | |
| 6,203,156 B1 | 3/2001 | Wu et al. | |
| 6,264,692 B1 | 7/2001 | Woffinden et al. | |
| RE37,585 E | 3/2002 | Mourou et al. | |
| 6,451,056 B1 * | 9/2002 | Cumming | 623/6.18 |
| 6,491,393 B1 | 12/2002 | Appleton | |
| 6,558,419 B1 | 5/2003 | Pham et al. | |
| 6,568,807 B2 | 5/2003 | Rogers et al. | |
| 6,592,621 B1 | 7/2003 | Domino | |
| 6,609,673 B1 | 8/2003 | Johnson | |
| 6,632,887 B2 | 10/2003 | LeBoeuf et al. | |
| 6,638,307 B2 | 10/2003 | Valyunin et al. | |
| 6,648,741 B2 | 11/2003 | Schneider | |
| 6,656,222 B2 | 12/2003 | Young et al. | |
| 6,857,744 B2 | 2/2005 | Nakada et al. | |
| 6,884,262 B2 | 4/2005 | Brady et al. | |
| 6,896,368 B2 | 5/2005 | Baugh | |
| RE38,839 E | 10/2005 | Magnante | |
| 6,997,554 B2 | 2/2006 | Nakada et al. | |
| 7,014,656 B2 | 3/2006 | Galin | |
| 7,053,997 B2 | 5/2006 | Suzuki et al. | |
| 2001/0034552 A1 | 10/2001 | Young et al. | |
| 2002/0026239 A1 | 2/2002 | Schachar | |
| 2003/0060880 A1 | 3/2003 | Feingold | |
| 2003/0093083 A1 | 5/2003 | Peyman | |
| 2004/0039446 A1 | 2/2004 | McNicholas | |
| 2004/0184158 A1 | 9/2004 | Shadduck | |
| 2004/0188872 A1 | 9/2004 | Jani | |
| 2005/0021139 A1 | 1/2005 | Shadduck | |
| 2005/0125056 A1 | 6/2005 | Deacon et al. | |
| 2005/0154456 A1 | 7/2005 | Brady et al. | |
| 2005/0177231 A1 | 8/2005 | Ricci et al. | |
| 2007/0274626 A1 * | 11/2007 | Sabeta | 385/24 |
| 2008/0077239 A1 | 3/2008 | Zickler et al. | |
| 2008/0281413 A1 | 11/2008 | Culbertson et al. | |
| 2008/0291392 A1 | 11/2008 | Sicari et al. | |
| 2010/0152846 A1 | 6/2010 | Vaillant et al. | |

FOREIGN PATENT DOCUMENTS

| | | |
|---|---|---|
| JP | 61223820 | 4/1986 |
| WO | WO0119290 A1 | 3/2001 |
| WO | WO02065951 A2 | 8/2002 |
| WO | WO 03000484 A1 | 1/2003 |
| WO | WO03037225 A1 | 5/2003 |
| WO | WO 2006012156 A1 | 2/2006 |

OTHER PUBLICATIONS

Matsushima H., et al., "Active Oxygen Processing for Acrylic Intraocular Lenses to Prevent Posterior Capsule Opacification," Journal of Cataract and Refractive Surgery, 2006, vol. 32 (6), pp. 1035-1040, Jul. 2006.

Zickler L., et al., "Ferntosecond All-Solid-State Laser for Refractive Surgery," Proceedings of SPIE, 2003, vol. 4978 (2003), pp. 194-207, Jun. 19, 2003.

* cited by examiner

MARK FOR INTRAOCULAR LENSES

BACKGROUND OF THE INVENTION

1. Field of the Invention

The present invention relates generally to intraocular lenses, and more specifically to intraocular lenses containing markings.

2. Description of the Related Art

Intraocular lenses are used replace or supplement the natural lens of an eye. Similar to other ophthalmic lenses, such as spectacles and contact lenses, intraocular lenses may be configured to provide both spherical and cylinder power. The cylinder power is used to correct rotational asymmetry astigmatism of the cornea or eye of a subject that degrades the vision of the eye and cannot be corrected by adjusting the spherical power of the lens. Lenses that are configured to correct astigmatism are commonly referred to as toric lenses.

The astigmatism of an eye or cornea may be characterized in terms of a magnitude in Diopters along an astigmatic axis. To correct this astigmatism, or at least reduce its magnitude, a toric lens is provided. As used herein, a toric lens is characterized by a base spherical power (which may be positive, negative, or zero) and a cylinder power that is added to the base spherical power of the lens for correcting the astigmatism of the eye. As used herein, a toric lens is also characterized by a "low power meridian" with a constant power equal to the base spherical power and an orthogonal "high power meridian" with a constant power equal to the base spherical power plus the cylinder power of the lens, To correct astigmatism of the eye, an angular orientation of the astigmatic axis of the cornea or eye is first determined, then a toric lens with a predetermined base spherical power and cylinder power is aligned so that the low power meridian of the toric lens is at the same angle as the astigmatic axis of the cornea or eye. When correct alignment between the axes of the lens and cornea is achieved, the astigmatism of the lens may cancel, or at least significantly reduce, the astigmatism of the cornea, resulting in improved vision over an intraocular lens having spherical correction only. While correct angular alignment between the astigmatic axis of the cornea and the low power meridian of the corrective lens is generally important for providing optimal correction, alignment is particular critical in the case of intraocular lenses, since it is much more difficult to replace or re-orient an intraocular lens once it has been placed into the eye.

In practice, there may be some residual astigmatism left in the eye due to a rotational misalignment between the astigmatic axis of the cornea and the low power meridian of the corrective intraocular lens. Mathematically, the astigmatism of the cornea (amount−A, orientation θ), plus an astigmatism of the rotationally misaligned lens (amount+A, orientation θ+δ), results in a residual astigmatism with magnitude 2A sin δ, oriented at 45° to the angle (θ+δ/2). As an example, consider a cornea that has 2 Diopters of astigmatism, and a lens that has 2 Diopters of cylinder power. If the lens is implanted with an angular error δ of 5 degrees, then the residual astigmatism is (2)(2 Diopters)(sin 5°)=0.35 Diopters. For a looser tolerance of 10 degrees, the residual astigmatism is (2)(2 Diopters)(sin 10°)=0.7 Diopters. A typical threshold for astigmatism is 0.25 Diopters, so that if the light reaching the retina has less than 0.25 Diopters of astigmatism, then the astigmatism does not significantly degrade the vision of the eye.

Accordingly, there is a need for toric intraocular lenses and methods of implanting such lenses that aid a surgeon in quickly and accurately aligning such lenses with the astigmatic axis of the cornea.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description. Each and every feature described herein, and each and every combination of two or more of such features, is included within the scope of the present invention provided that the features included in such a combination are not mutually inconsistent.

Embodiments of the present invention are generally directed to marks for lenses and related methods and systems for fabrication and use thereof. Marks according to embodiments of the present invention find particularly use as an aid in adjusting, measuring, or confirming the angular alignment of an ophthalmic lens in or on the eye of a human or animal subject. Accordingly, embodiments of the present invention may be advantageously incorporated into toric lenses as an aid to aligning a low power meridian of the lens with an astigmatic axis of the cornea or eye. Embodiments of the present invention are illustrated below with particular reference to intraocular lenses; however, other types of lenses fall within the scope of the present invention including, but not limited to, contact lenses, phakic intraocular lenses, corneal inlays or onlays, and the like.

As used herein, the term "clear aperture" or "optical zone" means the area of a lens or optic defining the extent of the lens or optic available for forming an image or focus from a collimated or distant light source. The clear aperture or optical zone is usually circular and specified by a diameter. The clear aperture or optical zone may have the same or substantially the same diameter as the optic or lens itself. Alternatively, the diameter of the clear aperture or optical zone may be smaller than the diameter of the optic, for example, due to the presence of a glare or PCO reducing structure disposed about a peripheral region of the optic.

As used herein, the term "visibility" means the property or capability of being readily noticed and/or identified.

Figure 1:
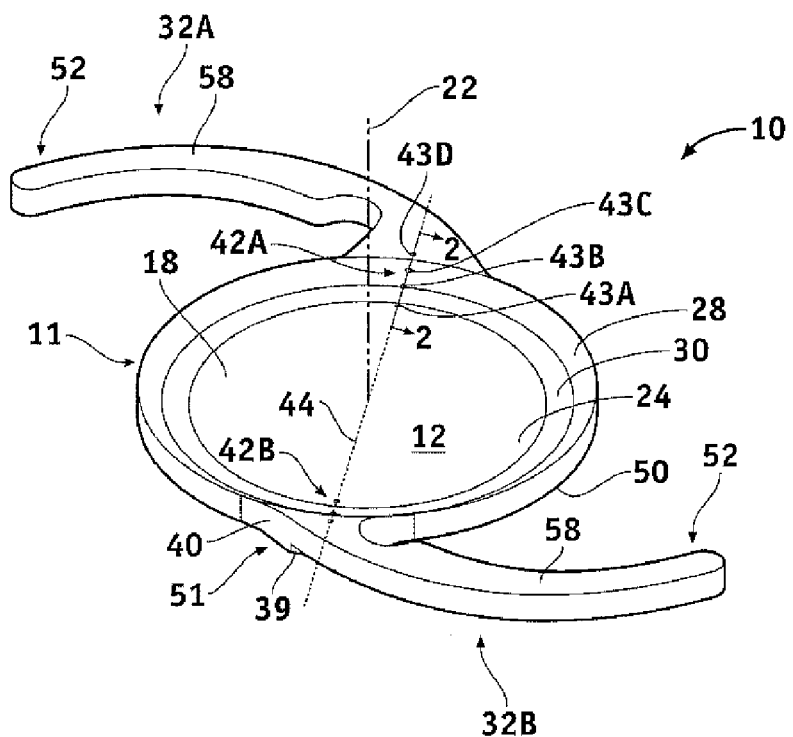
FIG. 1 is a perspective view illustrating the anterior surface of an intraocular lens according to an embodiment of the present invention.
Figure 2:
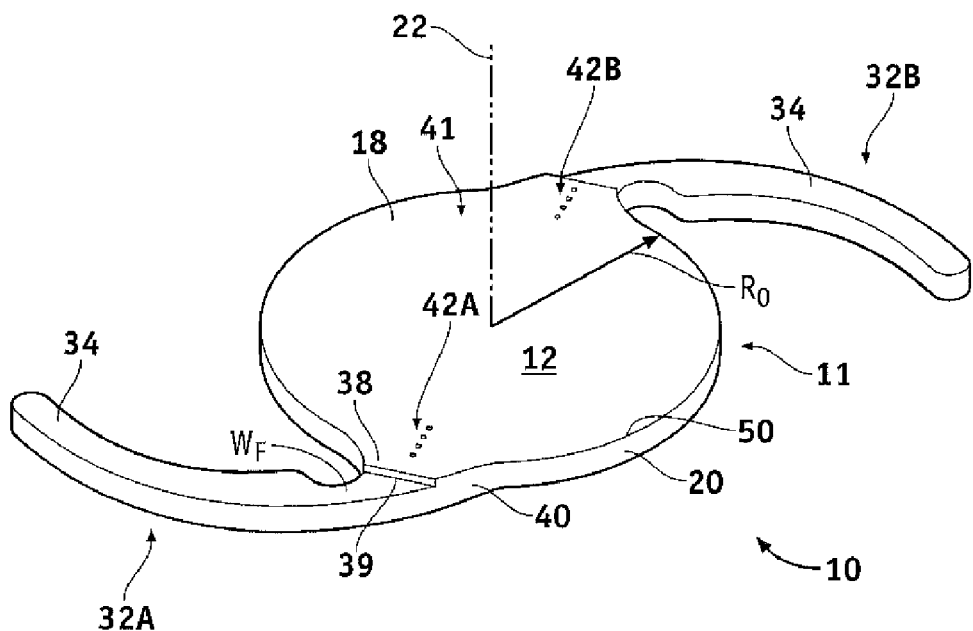
FIG. 2 is a perspective view illustrating the posterior surface of the intraocular lens shown in FIG. 1.
Figure 3:
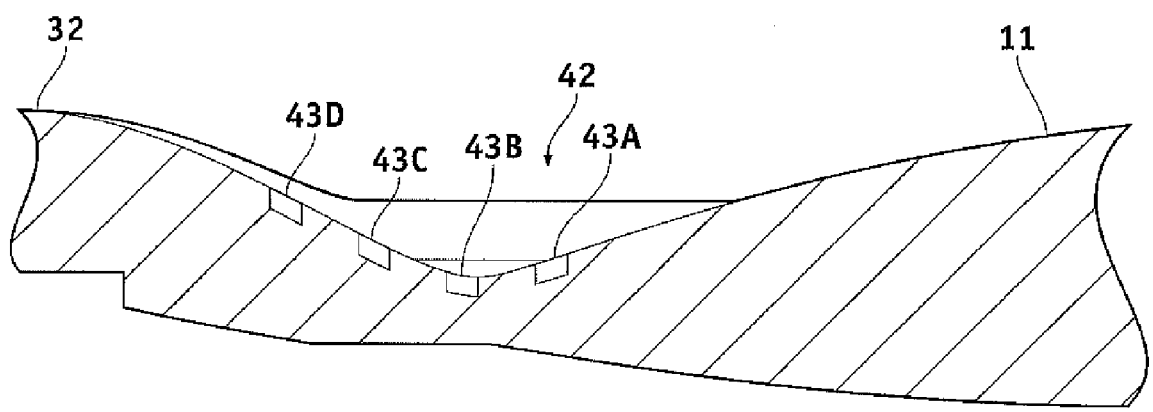
FIG. 3 is a side view of a portion of the intraocular lens shown in FIG. 1.

Referring to FIGS. 1-3, in one useful embodiment, a foldable intraocular lens 10 comprises an optic 11 including a clear aperture or an optical zone 12 and a peripheral zone 13 entirely surrounding the optical zone 12. The optic 11 has an anterior face 14, a substantially opposing posterior face 18, an optic edge 20, and an optical axis 22. The anterior face 14 comprises a central face 24, a peripheral face 28, and a recessed annular face 30 therebetween that is disposed posterior to the peripheral face 28. The intraocular lens 10 further comprises haptics 32 extending from the optic 11 that may optionally be integrally formed with the optic 11. Each haptic 32a, 32b comprises a distal posterior face 34, a proximal posterior face 38, and a step edge 39 disposed at a boundary therebetween. Each haptic 32a, 32b further comprises a side edge 40 disposed between the optic edge 20 and the step edge 39. The proximal posterior face 38 and the posterior face 18 of the optic 11 form a continuous surface 41. An edge corner 50 is formed by the intersection of the continuous surface 48 with the optic edge 20, the side edge 40, and the step edge 39. A more detailed description of at least some of the elements of intraocular lens 10 is found in U.S. Patent Application Publication 2005/0125056, which is herein incorporated by reference in its entirety as if fully set forth herein. While features of the optic 11 and haptics 32 include elements of certain embodiments of the present invention, other types of optic bodies and/or haptic structures are within the scope of the present invention.

The intraocular lens 10 also comprises a first mark 42a and a second mark 42b, which may be configured for use in angularly aligning the intraocular lens 10 in the eye, for example, when the intraocular lens 10 is a toric intraocular lens. In certain embodiments, each of the marks 42a, 42b is partially disposed within the optical zone 12 and partially disposed within the first haptic 32a and the second haptic 42b, respectively. Each mark 42a, 42b comprises four or more features, wherein the eight features 43 of the two marks 42 are disposed along, or form, an imaginary line 44 when viewed from the anterior side or the posterior side of the intraocular lens 10. When viewed from the anterior or posterior side of the intraocular lens 10, the features 43 may be in the form of small circles or dots, or any other shape considered useful, for example, to enhance the visibility of the features 43.

The features 43 in the illustrated embodiment are located at increasing radii from one another, with the feature 43a located within the optical zone 12, the feature 43b located within the recessed annular face 30, the feature 43c located within the peripheral face 28, and the feature 43d located at the greatest radial distance and within the haptic 32. Alternatively, feature 43a may also be located within the recessed annular face 30 and/or the feature 43d may be located within the optic 11 rather than the haptic 32 (e.g., within the peripheral face 28); however, the inventors have found that the visibility of the marks 42 are generally increased or enhanced by meeting certain extent and/or spacing criteria discussed in greater detail below herein. Thus, the diameter of the central face 24 and/or the diameter of optic 11 may make it advantageous to locate feature 43a within the optical zone 12 and/or to locate feature 43d within the haptic 32.

In the illustrated embodiment, optic 11 is generally circular having a radius $R_o$ and may be constructed of at least one of the materials commonly used for resiliently deformable or foldable optics, such as silicone polymeric materials, acrylic polymeric materials, hydrogel polymeric materials, such as polyhydroxyethylmethacrylate, polyphosphazenes, polyurethanes, and mixtures thereof and the like. Alternatively, the optic 11 may be constructed of at least one of the commonly employed material or materials used for rigid optics, such as polymethylmethacrylate (PMMA). In some embodiments, the optic 11 is made of SENSAR® brand of acrylic. Other advanced formulations of silicone, acrylic, or mixtures thereof are also anticipated. The optic 11 material is preferably selected such that the optical zone 12 is optically clear and exhibits bio compatibility in the environment of the eye. Foldable/deformable materials are particularly advantageous since optics made from such deformable materials may be rolled, folded or otherwise deformed and inserted into the eye through a small incision. The lens material preferably has a refractive index allowing a relatively thin, and preferably flexible optic section, for example, having a center thickness in the range of about 150 micrometers to about 1000 micrometers, depending on the material and the optical power of the optic 11. For example, in one embodiment, the optic 11 is made of Sensar® brand of acrylic and an optical power of 20D. In such embodiment, the optical zone 12 has a center thickness $T_c$ that is preferably in the range of about 0.5 millimeter or less to about 1.0 millimeter or more, more preferably in the range of about 0.7 millimeter to about 0.9 millimeter. The center thickness $T_c$ may vary from these ranges depending on factors such as the lens material and the dioptric power of the optical zone 12. The optic 11 preferably has a diameter of at least about 4 millimeter to about 7 millimeter or more, more preferably about 5 millimeter to about 6.5 millimeter or about 6.0 millimeter. As used herein the term "thickness" generally refers to a dimension of a portion or feature of the intraocular lens 10 as measured substantially along the optical axis 22.

The intraocular lens 10 may comprise any of the various means available in the art for centering or otherwise locating or supporting the optical zone 12 within the eye. In the illustrated embodiment a pair of haptics 32 are used for centering the intraocular lens 10 within the eye; however, other types of support structure may be used, for example, as typically used for supporting an optic or optics of an accommodating intraocular lens. The haptics 32 of the illustrated embodiment may be integrally formed of the same material as the optic 11 to form a one-piece IOL. Alternatively, the haptics 32 may be integrally formed in a common mold with the optic 11, but be made of a different material than the optic 11. In other instances, the haptics 32 formed of the same material as the optic 11, but haptics 32 and the optic 11 materials have different states, for instance differing amounts of water content or percentage of cross-linked polymer. Additionally or alternatively, the haptics 32 may be formed separately from, of the same or a different material as, the optic 11 and subsequently attached to the optic 11 to provide a three-piece configuration. The haptics 32 may comprise any of a variety of materials which exhibit sufficient supporting strength and resilience, and which are substantially biologically inert in the intended in vivo or in-the-eye environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In other embodiments, the intraocular lens 10 comprises a positioning means that allows the optic 11 to move along the optical axis 22 or be deformed in response to deformation of the capsular bag and/or in response to the ciliary muscles of the eye.

The optical zone 12 may take any form suitable for providing vision to a subject. For example the optical zone 12 may be biconvex, plano-convex, plano-concave, meniscus, or the like. The optical power of the optical zone 12 may be either positive or negative. The general profile or shape of the posterior face 18 and the central face 24 of the optical zone 12 may be any used for producing an optic based on refraction of incident light. For instance, the posterior face 18, the central face 24, or both faces 18, 24 may be spherical with an overall radius of curvature that is either positive or negative. Alternatively, the profile or shape of either the posterior face 18, the central face 24, or both faces 18, 24 may be parabolic or any aspheric shape common in the art for reducing aberrations such as spherical aberrations. For example, the posterior face 18 or the central face 24 may be an aspheric surface designed to reduce spherical aberrations based on either an individual cornea or group of corneas as described by Piers et al, in U.S. Pat. No. 6,609,673 and U.S. patent application Ser. Nos. 10/119,954, 10/724,852, herein incorporated by reference. Other aspheric and asymmetric surface profiles of the posterior face 18 or the central face 24 of use within the art are also consistent with embodiments of the intraocular lens 10. The posterior face 18 or the central face 24 may alternatively be configured to provide more than one focus, for example to correct for both near and distant vision as described by Portney in U.S. Pat. No. 4,898,461. The optical zone may be configured as part of a lens system (e.g., a two optic system) and/or for providing accommodative vision (e.g., by being made of a material that can change shape to provide varying optical power in response to an ocular force).

At least portions of the posterior face 18, the central face 24, or both faces 18, 24 of the optical zone 12 may comprise one or more optical phase plates. In such embodiments, the total optical power of the optical zone 12 is a combination of the refractive power of the posterior face 18 and the central face 24, and the optical power of the one or more diffraction orders produced by the one or more phase plates. The one or more phase plates may be either a monofocal phase plate providing one dominant diffraction order or a multifocal phase plate, such as a bifocal phase plate, for providing, for instance, simultaneous near and distant vision. Other types of phase plates may also be used. For example, the phase plate may be based on a change in the refractive index of the material used to form the optical zone 12.

The total optical power of the optical zone 12 is preferably within a range of at least +2 Diopters to +50 Diopters or more, more preferably within a range of +5 Diopters to +40 Diopters, and most preferably a range of +5 Diopters to +30 Diopters. The total optical power may be either positive or negative, for instance within a range of −15 Diopters or to +50 Diopters or more, or within a range of −10 Diopters to +40 Diopters. Other ranges of refractive optical power may be preferred, depending on the particular application and type of intraocular lens to be used.

In certain embodiments, each haptic 32a, 32b is characterized by a haptic thickness that is equal to a distance, as measured along the optical axis 22, between the distal posterior face 34 of the haptic 32 and the substantially opposing anterior face 58. The haptic thickness may be greater than or approximately equal to a thickness of the optic edge 20, as measured along the optical axis 22. The thicknesses may be selected based on the particular material from which the intraocular lens 10 is made, the amount of rigidity desired, the optical power of the lens 10, and other such factors. In some embodiments, at least one of the haptic thickness and the optic edge thickness, is preferably in the range of about 0.2 millimeter or less to about 1 millimeter or more, more preferably in the range of about 0.3 millimeter to about 0.6 millimeter, and even more preferably in the range of about 0.4 millimeter to about 0.5 millimeter.

The step edge 39 is disposed between the proximal posterior face 38 and distal posterior face 34 of each haptic 32a, 32b. The step edge 39 is part of the edge corner 50 that forms a continuous boundary around the posterior face 18 of the optic 11 to help prevent PCO. In certain embodiments, the step edge 39 has a height H that is in the range of 0.05 millimeter or to 1 millimeter or more. In other embodiments, the step edge 39 has a height H that is in the range of 0.2 millimeter to 0.5 millimeter.

As a result of the step edge 39, the distal posterior face 34 of each haptic 32a, 32b may have an anterior offset relative to the proximal posterior face 38. In certain embodiments, the step edge 39 has a height H that is much less than the optic edge thickness $T_o$. For example, the height H may be about 0.1 millimeter and the optic edge thickness $T_o$ may be in the range of about 0.4 millimeter or less to about 0.5 millimeter or more. Alternatively, in other embodiments, the height H is greater than or approximately equal to the optic edge thickness $T_o$. The height H may be selected based on various design parameters, including, the particular material from which the intraocular lens 10 is made, the amount of rigidity desired in the haptics 32, and other such factors. Preferably, height H is selected sufficiently large so that the integrity of the contact of the edge corner 50 with the posterior capsule of the eye is maintained so as to help avoid PCO.

As illustrated in FIG. 3, in certain embodiments, the distal posterior face 34 of each haptic 32a, 32b is perpendicular to the optical axis 22. In other embodiments, each haptic 32a, 32b further comprises an anterior face 58 that is also substantially perpendicular to the optical axis. In such embodiments, the step edge 39 produces an offset relationship between the distal portion 52 of the haptics 32 and the peripheral zone 13. This offset relationship may be favorably used to convert the radial force of the ciliary muscles of the eye on the haptics 32 into an axial force that biases or pushes the posterior face 18 of the optic 11 in a posterior direction along the optical axis 22 and against the posterior capsule of the eye. This is accomplished without the need for angled haptics, which can be more difficult and/or expensive to manufacture than when the distal posterior face 34, the anterior face 58, or both the distal posterior face 34 and the anterior face 58 are manufactured substantially perpendicular to the optical axis. Alternatively, the haptics 32 may be manufactured such that the distal posterior face 34 and/or the anterior face 58 are disposed at an angle relative to a plane perpendicular to the optical axis 22. This configuration may be used to increase the amount of posterior bias or force on the posterior face 18 of the optic 11 against the posterior capsule. In such configuration the angle is preferably in the range of about 2 degrees or less to at least about 12 degrees.

With additional reference to FIG. 4, which is a plan view of the intraocular lens 10 from the posterior side, various elements, features, and advantages of the marks 42 will be discussed in greater detail.

The inventors have found that non-continuous marks comprising distinct features, such as the features 43 shown in FIGS. 1-4, to have advantages over continuous marks such as lines. For example, a continuous line that perpendicular to the haptic-optic junction may allow residual cells to migrate onto to the anterior optic after cataract surgery (e.g., the "groove" may provide contact guidance to cells). Non-continuous marks do not provide contact guidance, dependent on the spacing on the marks, size of the marks, etc.

Figure 4:
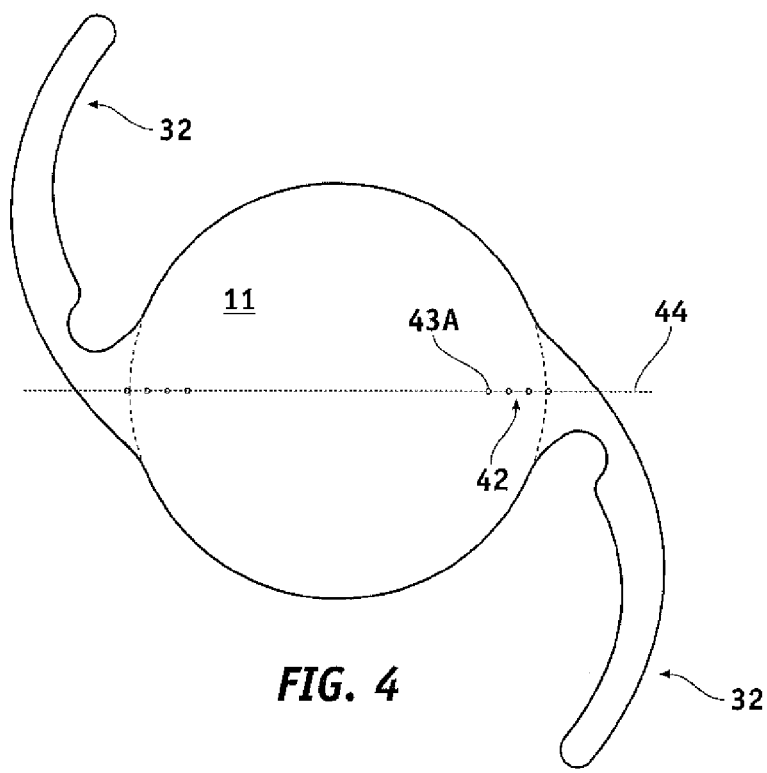
FIG. 4 is a plan view of the posterior side of the intraocular lens shown in FIG. 1.

As seen in FIG. 4, each mark 42 comprises four features 43 for a total of eight features 43. The features 43 are disposed along, or form, the imaginary line 44 and are collinear when viewed from the posterior side of intraocular lens 10. Additionally or alternatively, the eight features 43 may all be coplanar, for example, within a plane that is parallel to and contains the optical axis 22. The features 43 are not necessarily collinear when viewed from other directions, for example, when viewed in a plane that is parallel to and contains the optical axis 22, as seen in FIG. 3.

The features 43 of the illustrated embodiment are configured as holes disposed along the anterior surface 14 that are circular when viewed from the anterior side of the intraocular lens 10. Alternatively, some or all of the features 43 may be disposed along the posterior face 18 or may be through holes extending from the anterior face 14 to the posterior face 18. In some embodiments, one or both the features 43 is disposed within or inside intraocular lens 10 between the anterior and posterior faces 14, 18. For example, one or more of the features 43 may be formed using a laser, such as a femtosecond laser, as disclosed in U.S. Patent Application Publication Number 2008/077239, which is herein incorporated by reference in its entirety.

In the illustrated embodiment, holes 43 are circular and have a diameter of 85 micrometers or about 85 micrometers (e.g. 85 micrometers plus or minus 15 micrometers), and a depth of 50 micrometers or about 50 micrometers (e.g. 50 micrometers plus or minus 15 micrometers). In certain embodiments, the holes 43 have a depth that ranges from 25 micrometers to 100 micrometers and/or a diameter that ranges from 25 micrometers to 100 micrometers. In certain embodiments, one or more of the features 43 has a shape that is non-circular when viewed from the anterior or posterior side of the intraocular lens 10. For example, one or more of the features 43 may be square, rectangular, triangular, oval, or the like, when viewed from the anterior or posterior side of the intraocular lens 10.

In the illustrated embodiment, each of the marks 42 has a radial extent that is from 1.4 millimeters to 1.6 millimeters for a typical optic diameter of an intraocular lens for human implantation. As used herein, a "typical optic diameter" (for an intraocular lens for human implantation) means having a diameter that is between 4 millimeters and 7 millimeters. The inventors have found visibility of the marks 42 may be enhanced or increased under typical microscope viewing conditions when each mark 42 has a radial extent that is at least about 1.5 millimeters for a typical optic diameter, for example, at least 1.4 millimeters, 1.5 millimeters, or 1.6 millimeters. In certain embodiments, each mark 42 has 5 features, 6 features, or more than 6 features disposed collinearly, wherein the radial extent of marks 42 is at least about 1.5 millimeters for a typical optic diameter. The inventors have found that visibility of the marks 42 under typical microscope viewing conditions is enhanced or increased when each mark 42 contains at least 4 features, dots, or holes 43 and that configurations in which a mark contains only three features, dots, or holes result in reduced visibility of such marks compared to marks having at least 4 features, dots, or holes. As used herein "typical microscope viewing conditions" means an operating surgical microscope with a magnification of 5× to 35×, or a slit lamp with a magnification of 10× to 30×.

The inventors have also found that visibility is increased or enhanced under typical microscope viewing conditions when each mark 42 has a maximum radial location from the optical axis 22 that is at least 2.9 millimeter, preferably at least 3.0 millimeters or at least 3.1 millimeters. In some embodiment, the maximum radius of each mark 42 extends outside the optic 11, for example, into the haptics 32 in the illustrated embodiment of FIGS. 1-4. Visibility of the marks 42 may also be increased or enhanced under typical microscope viewing conditions when each mark 42 has a minimum radius from the optical axis 22 that is less than or equal to 2.3 millimeter or less than or equal to 2.2 millimeters.

The visibility of marks 42 may also be increased or enhanced by providing a maximum spacing between adjacent features 43 that is below a certain limit, for example, when a maximum center-to-center spacing between adjacent features 43 is less than or equal to 600 micrometers for the features 43 having a diameter that is from 25 micrometers to 100 micrometers, or preferably 50 micrometers to 100 micrometers when viewed from the anterior side. In some embodiments, the features 43 of each mark 42 are evenly spaced along the imaginary line 44 and have a spacing between adjacent features that is from 450 micrometers to 550 micrometers. In certain embodiments, the spacing between at least some of the adjacent features 43 is greater than a predetermined minimum. For example, it has been found that cell migration along the mark 42 may be when the spacing between adjacent edges of adjacent features 43 is at least 20 micrometers or at least 50 micrometers. The minimum spacing to inhibited, reduced, or eliminated has been found to depend on factors such as the material from which the intraocular lens is made.

Each feature 43 may have a flat or generally flat bottom, as illustrated in FIG. 3. The bottoms of one or more of the feature 43 may extend in a direction that is perpendicular to the optical axis 22. Alternatively, the bottom of one or more feature 43 may extend at an angle to the optical axis 22, for example, at an angle that is parallel or approximately parallel to the local angle of the face into which each feature 43 is disposed, as illustrated in FIG. 3. Rather than being flat, the bottom of each feature 43 may be curved, for example, being concave or convex to focus light. The curved bottoms, or other bottom configurations, may be configured to increase visibility of each feature 43 and/or each mark 42, for example, by focusing incident light. The use of roughening, fluorescent materials, and the like may be use on the bottom and/or sides of features 43 to enhance visibility.

High visibility or easily detectable marks 42 may be of particular importance when the angular orientation of intraocular lens 10 is more critical, for example, when intraocular lens 10 is a toric intraocular lens. In such embodiments, toric intraocular lens 10 has an low power meridian disposed along the imaginary line 44. Alternatively, the imaginary line 44 may be disposed along a high power meridian of intraocular lens 10. In some embodiments, the imaginary line 44 is disposed at some other predetermined angle relative to the low power or high power meridian of intraocular lens 10, for example, at a 45 degree angle to the high power meridian of intraocular lens 10.

EXAMPLE

Figure 5:
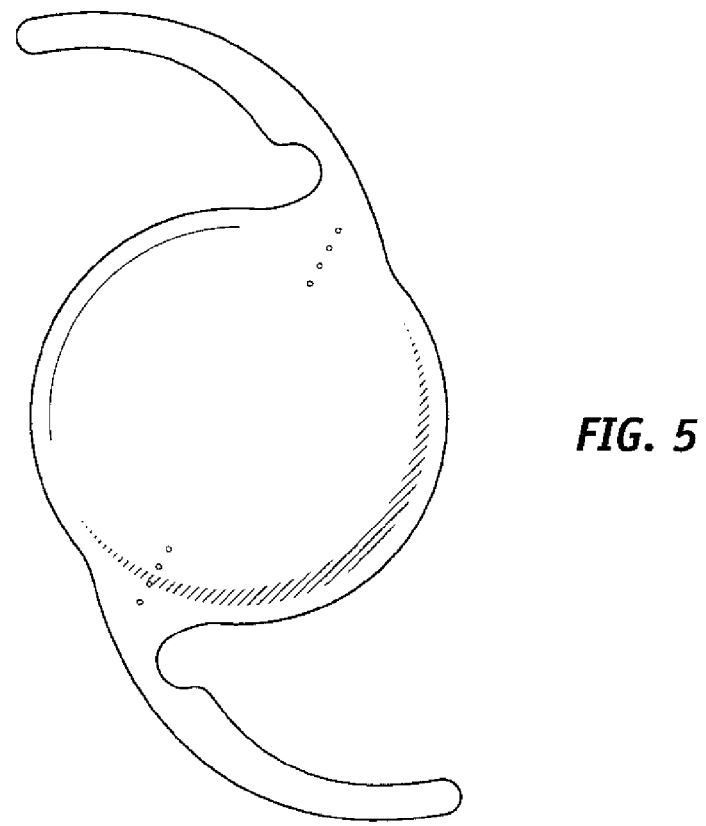
FIG. 5 is a plan view of the anterior side of an intraocular lens made according to an embodiment of the present invention.

Toric intraocular lenses were produced having various mark geometries. The toric intraocular lenses each had an aspheric toric surface on the anterior surface of the lens with low power meridian orientation marks to assist a surgeon with positioning the intraocular lens along a correct meridian upon implantation in the eye. The inventors found that meridian orientation marks on a toric intraocular lens provided best visibility and ease of use in aligning the intraocular lens when each of two marks comprised 4 features or dots on each mark. Each feature was approximately 85 micrometers in diameter and comprised a circular hole in the anterior surface with a depth of about 50 micrometers. The four features of each mark were located at diameters of 4.5, 5.0, 5.5 and 6.0 millimeter on the anterior surface of the IOL. A toric intraocular lens with this geometry will be referred to herein as a "reference lens" or "reference intraocular lens". Similarly, this geometry will be referred to as the "Reference Geometry". The reference lens describe here is generally represented by FIGS. 1-4. A photograph of a toric photograph of a toric intraocular lens with this geometry is shown in FIG. 5.

In arriving at the reference lens, various alternative mark geometries were also considered and evaluated:

1) 4 features on anterior surface (×2) (4.5, 5.0, 5.5, 6.0 millimeter diameters)—reference geometry.
2) 4 features on anterior surface (×2) (4.0, 4.5, 5.0, 5.5 millimeter diameters)
3) 3 features on anterior surface (×2) (4.5, 5.0, 5.5 millimeter diameters)
4) 3 features on posterior surface (×2) (4.5, 5.0, 5.5 millimeter diameters)
5) Line from 4.5-5.5 millimeter diameters on anterior surface (×2)
6) 5 features to form a "T" (×2)
7) 5 features to form a "+" (×2)

In the end, reference intraocular lenses having Geometry 1 were found to provide the best performance in terms of ease of use, visibility with the surgical microscope and slit lamp biomicroscope, clinical acceptability, and lack of cellular deposits or deposits. The intraocular lenses with the Reference Geometry provided various advantages over the markings commercially available on conventional toric intraocular lenses, including:

The non-continuous geometry of the marks on the reference intraocular lens can have advantages over continuous marks as discussed above herein.

The marks of the reference intraocular lens can be easily identified and used under a typical operating microscope or slit lamp biomicroscope. The surgeon can easily see the reference lens markings to align it in the eye with the steep axis of the cornea.

The marks of the reference intraocular lens are visible after tumbling and do not have to have sharp features. It was found that sharp edges on marks are not necessary and that the profile of the marks of the reference intraocular lens can be a punch, dimple, or v-notch.

While the markings of the reference intraocular lens may alternatively be created on the posterior surface, it was found that markings on the anterior surface were more compatible with other optic technologies, such as multifocal surfaces, which may preferably be formed on the posterior optic surface.

Various studies were conducted based on geometries 1-7 listed above to obtain the preferences of various ophthalmic surgeons/scientists in the field. The ophthalmologists used in these various studies are herein referred to as Dr. A through Dr. K.

In a first study, the marking geometries 1-7 were shared with Dr. A. Dr. A preferred the following in vitro:

4 features on anterior surface (×2) (4.5, 5.0, 5.5, 6.0 millimeter diameters)—Reference Geometry.
Line from 4.5-5.5 millimeter diameters on anterior surface (×2).

However, upon implanting these intraocular lenses in a rabbit eye, Dr. A preferred the 4 features of the reference intraocular lens. An early prototype of the reference intraocular lens was implanted in the eye of a NZW rabbit for up to 5 weeks. The markings of the implanted intraocular lens were visible and no cell growth or deposits were seen in the markings. An SEM photomicrograph of this lens shown in FIG. 5.

In a second study, eight additional evaluations were conducted in which the eight ophthalmic surgeons/scientists were shown 3 different size marks and three prototypes based on three of the geometries listed above:

Geometry 1 (Reference Geometry): 4 features on anterior surface (×2) (4.5, 5.0, 5.5, 6.0 millimeter diameters).
Geometry 3: 3 features on anterior surface (×2) (4.5, 5.0, 5.5 millimeter diameters).
Geometry 4: 3 features on posterior surface (×2) (4.5, 5.0, 5.5 millimeter diameters).

The results were as follows:
Dr. B: preferred 4 features on anterior surface.
Dr. C: preferred 4 features on anterior surface.
Dr. D: preferred 4 features on anterior surface.
Dr. E: preferred 4 features on anterior surface (extra feature helps with alignment).
Dr. F: preferred 4 features on anterior surface.
Dr. G: opined that 2 features are enough to create a line and 3 features can be toric standard.
Dr. H: preferred 4 features on anterior surface.
Dr. I: preferred 4 features on anterior surface.

In a third study, confirmation of the higher visibility and preference of the reference intraocular lens design was obtained. In this third study, ophthalmic surgeons/scientists were shown the prototype of the marking configuration of 4 pairs of features (approximately 85 micrometers in diameter with a depth 50 micrometers) at 4.5, 5.0, 5.5 and 6.0 millimeter diameters on the anterior surface of the IOL. The results were as follows:

All ophthalmic surgeons thought that the markings for the Reference Geometry were very visible and clinically acceptable.
Dr. A: Confirmed preference of 4 features on anterior surface with the dimensions.
Dr. F: Confirmed preference of 4 features on anterior surface with the dimensions.
Dr. J: Confirmed preference of 4 features on anterior surface with the dimensions.
Dr. K: Confirmed preference of 4 features on anterior surface with the dimensions.

The 4th feature at 6 millimeter of the reference intraocular lens geometry was found to help in alignment by more readily drawing the doctors' eye to it. Once a doctor's eye was drawn to the 4th feature of the reference intraocular lens, this also helped in seeing the other marks.

Various affects may account for the unexpected preference for lenses having the Reference Geometry (4 features on anterior surface located at 4.5, 5.0, 5.5, 6.0 millimeter diameters) compared to those having Geometry 2 or 3 above (3 features located at 4.5, 5.0, 5.5 millimeter diameters). One explanation for this preference is that the second features of the Reference Geometry are located in the "gunnel" on the anterior surface of the optic of the reference intraocular lens (e.g., recessed annular face 30 shown in FIG. 1), while the fourth features are located on the haptics. Thus, the fourth feature of each mark has a raised height relative to the second feature located in the gunnel. This depth difference is greater than that between the second feature and the adjacent first and third features of Geometry 3 or 4. Thus, the larger difference in depth between the second and fourth features for the Reference Geometry cause difference in defocus of second and fourth features (when observed under a microscope) that may be more readily perceived by an observer, either consciously or subconsciously.

Also, as a result of the larger extent of the four features of the Reference Geometry compared to the 3 features of Geometry 2 or 3, the addition of the fourth features at a 6 millimeter diameter gives a higher probability that both marks would be within the field of view if the intraocular lens is de-centered.

The loss of mark or feature perception due to decentering may be particularly important in light various visual psychophysics affects. For example, under typical microscope viewing conditions, the light level is relatively low and, therefore, a microscope observer's eye has a higher reliance on the rods of the retina than on the cones. In contrast to the cones, the rods of the human eye have a relatively low density on-axis (center of the fovea). The cone density rapidly increased to a maximum at about 12-15 degrees off axis before then gradually becoming less dense at larger fields of view. A higher cone density correlates to higher visual sensitivity. As an intraocular lens becomes more de-centered under the microscope, one of the two marks moves closer to the center of the field of view where the observer's eye is actually less sensitive, while the other mark move to the periphery, where perception also decreases. Thus, the fourth feature of a de-centered intraocular lens having the Reference Geometry advantageously increases the probability that at least this fourth feature will be noticed on the mark that moves into the center of the field of view, since the fourth feature will still be in a relatively sensitive portion of the retina compared to the third feature of Geometry 3 or 4 above (which would be closer to the center of the retina, where visual sensitivity is less).

The above studies show that the reference lens (Geometry 1, having marks including four features and a relatively long radial extent) is strongly preferred by experienced ophthalmic surgeons/scientists over a similarly configured toric intraocular lens having only three features, a shorter extent for each mark, and a small total radial extent of the two marks (geometries 3 and 4). The strong preference for the reference intraocular lens design incorporating Geometry 1 was unexpected, which may be the result of one or more of the factors discussed above.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An intraocular lens having an anterior side and a posterior side, comprising:
    an optic body including an optical zone and a peripheral zone disposed about the optical zone, the optic body having an anterior face, an opposing posterior face, an optic edge, and an optical axis, the optic zone configured for forming an image from light incident on the faces;
    first and second haptics extending from the optic body;
    first and second marks, the first mark partially disposed within the optical zone and partially disposed within the first haptic and the second mark partially disposed within the optical zone and partially disposed within the second haptic, each mark comprising four features;
    wherein the eight features of the first and second marks are disposed along an imaginary line when viewed from the anterior side; and
    wherein the four features of each of the marks are evenly spaced along the imaginary line, the spacing between adjacent features being from 450 micrometers to 550 micrometers.

2. The intraocular lens of claim 1, wherein the optical axis and the eight features are coplanar.

3. The intraocular lens of claim 1, wherein the imaginary line is a straight line.

4. The intraocular lens of claim 1, wherein the features are circular when viewed from the anterior side.

5. The intraocular lens of claim 1, wherein one or more of the features are disposed on the anterior face of the optic body.

6. The intraocular lens of claim 1, wherein each of the features is a hole located along at least one of the faces.

7. The intraocular lens of claim 6, wherein at least one of the holes is a through hole.

8. The intraocular lens of claim 6, wherein each of the holes has a depth that is from 25 micrometers to 100 micrometers.

9. The intraocular lens of claim 6, wherein each of the holes has a bottom that is curved.

10. The intraocular lens of claim 1, wherein each of the features has a diameter that ranges from 50 micrometers to 100 micrometers when viewed from the anterior side.

11. The intraocular lens of claim 1, wherein the marks are disposed between the faces.

12. The intraocular lens of claim 1, wherein the marks each have an extent that is from 1.4 millimeters to 1.6 millimeters.

13. The intraocular lens of claim 1, wherein the marks each have an extent that is at least 1.5 millimeters.

14. The intraocular lens of claim 1, wherein each of the marks has a maximum radius from the optical axis that is at least 2.9 millimeters.

15. The intraocular lens of claim 14, wherein each of the marks has a minimum radius from the optical axis that is less than or equal to 2.3 millimeters.

16. An intraocular lens having an anterior side and a posterior side, comprising:
    an optic body including an optical zone and a peripheral zone disposed about the optical zone, the optic body having an anterior face, an opposing posterior face, an optic edge, and an optical axis, the optic zone configured for forming an image from light incident on the faces;
    first and second haptics extending from the optic body;
    first and second marks, the first mark partially disposed within the optical zone and partially disposed within the first haptic and the second mark partially disposed within the optical zone and partially disposed within the second haptic, each mark comprising four features;
    wherein the eight features of the first and second marks are disposed along an imaginary line when viewed from the anterior side; and
    wherein the intraocular lens is a toric intraocular lens having a high power meridian and the imaginary line is disposed along one of a line parallel to the high power meridian, a line perpendicular to the to the high power meridian, and a line oriented at an angle of 45 degrees from the high power meridian.

17. The intraocular of claim 16, wherein the optical axis and the eight features are coplanar.

18. The intraocular of claim 16, wherein the imaginary line is a straight line.

19. The intraocular of claim 16, wherein the features are circular when viewed from the anterior side.

20. The intraocular of claim 16, wherein one of more of the features are disposed on the anterior face of the optic body.

21. The intraocular of claim 16, wherein each of the features is a hole located along at least one of the faces.

22. The intraocular of claim 21, wherein at least one of the holes is a through hole.

23. The intraocular of claim 21, wherein each of the holes has a depth that is from 25 micrometers to 100 micrometers.

24. The intraocular of claim 21, wherein each of the holes has a bottom that is curved.

25. The intraocular of claim 16, wherein each of the features has a diameter that ranges from 50 micrometers to 100 micrometers when viewed from the anterior side.

26. The intraocular of claim 16, wherein the four features of each of the marks are evenly spaced along the imaginary line, the spacing between adjacent features being from 450 micrometers to 550.

27. The intraocular of claim 16, wherein the marks are disposed between the faces.

28. The intraocular of claim 16, wherein the marks each have an extent that is from 1.4 millimeters to 1.6 millimeters.

29. The intraocular of claim 16, wherein the marks each have an extent that is at least 1.5 millimeters.

30. The intraocular of claim 16, wherein each of the marks has a maximum radius from the optical axis that is at least 2.9 millimeters.

31. The intraocular of claim 30, wherein each of the marks has a minimum radius from the optical axis that is less than or equal to 2.3 millimeters.

* * * * *